(12) United States Patent
Amato (10) Patent No.: US 9,883,805 B2
(45) Date of Patent: Feb. 6, 2018

(54) PROCEDURE FOR DENTAL AESTHETIC ANALYSIS OF THE SMILE AREA AND FOR FACILITATING THE IDENTIFICATION OF DENTAL AESTHETIC TREATMENTS

(71) Applicant: Aldo Amato, Padua (IT)

(72) Inventor: Aldo Amato, Padua (IT)

( * ) Notice: Subject to any disclaimer, the term of this patent is extended or adjusted under 35 U.S.C. 154(b) by 96 days.

(21) Appl. No.: 14/761,601

(22) PCT Filed: Feb. 4, 2013

(86) PCT No.: PCT/IB2013/050925
§ 371 (c)(1),
(2) Date: Jul. 16, 2015

(87) PCT Pub. No.: WO2014/114991
PCT Pub. Date: Jul. 31, 2014

(65) Prior Publication Data
US 2015/0351638 A1    Dec. 10, 2015

(30) Foreign Application Priority Data
Jan. 23, 2013   (IT) .............................. PD2013A0010

(51) Int. Cl.
| A61B 5/00 | (2006.01) |
| A61B 6/14 | (2006.01) |
| A61B 6/00 | (2006.01) |
| A61C 13/00 | (2006.01) |
| A61C 19/05 | (2006.01) |
| A61C 7/00 | (2006.01) |

(52) U.S. Cl.
CPC .......... *A61B 5/0088* (2013.01); *A61B 5/0013* (2013.01); *A61B 5/743* (2013.01); *A61B 6/14* (2013.01); *A61B 6/5217* (2013.01); *A61C 7/002* (2013.01); *A61C 13/0004* (2013.01); *A61C 19/05* (2013.01)

(58) Field of Classification Search
CPC ..... A61B 5/0088; A61B 5/0013; A61B 5/743; A61B 6/14; A61B 6/5217; A61C 7/002; A61C 13/0004; A61C 19/05
See application file for complete search history.

(56) References Cited

U.S. PATENT DOCUMENTS 5,278,756 A * 1/1994 Lemchen ............... A61C 19/04
128/920
5,605,459 A * 2/1997 Kuroda .............. A61C 13/0004
433/213

(Continued)

*Primary Examiner* — Manav Seth
(74) *Attorney, Agent, or Firm* — Themis Law (57) ABSTRACT

The invention is a method for the aesthetic analysis of the teeth in the smile area, suited to facilitate the identification of aesthetic dental treatments and including: photographic examination of the patient's teeth; calibration of the images as a function of certain measures taken; consistency check of the data to detect and limit errors due to incorrect measurements; identification on the calibrated images of a defined set of reference points; automatic analysis and parametrization of the images with respect to the reference points; determination of possible treatments suited to achieve the desired aesthetic improvement; and display and/or print representation of the resulting possible treatments.

13 Claims, 4 Drawing Sheets

(56) References Cited

U.S. PATENT DOCUMENTS

| | | | | |
|---|---|---|---|---|
| 5,659,625 A * | 8/1997 | Marquardt | ......... | G06K 9/00281 |
| | | | | 345/634 |
| 5,683,243 A * | 11/1997 | Andreiko | ................ | A61C 7/00 |
| | | | | 433/24 |
| 5,851,115 A * | 12/1998 | Carlsson | .............. | A61C 9/0053 |
| | | | | 433/215 |
| 6,152,731 A * | 11/2000 | Jordan | ................ | A61C 13/0004 |
| | | | | 433/69 |
| 6,227,850 B1 * | 5/2001 | Chishti | .................... | A61C 7/00 |
| | | | | 433/213 |
| 6,318,994 B1 * | 11/2001 | Chishti | .................... | A61C 7/00 |
| | | | | 433/213 |
| 6,350,120 B1 * | 2/2002 | Sachdeva | ................. | A61C 7/00 |
| | | | | 433/24 |
| 6,616,444 B2 * | 9/2003 | Andreiko | ................. | A61C 7/00 |
| | | | | 433/3 |
| 7,013,191 B2 | 3/2006 | Rubbert | | |
| 7,613,527 B2 * | 11/2009 | Raby | ........................ | A61C 7/00 |
| | | | | 433/2 |
| 8,650,005 B2 * | 2/2014 | Liao | .................... | G09B 23/283 |
| | | | | 703/1 |
| 9,345,553 B2 * | 5/2016 | Andreiko | ............... | A61C 7/002 |
| 9,579,057 B2 * | 2/2017 | Bradu | ................. | A61B 5/4839 |
| 2004/0197727 A1 | 10/2004 | Sachdeva | | |
| 2011/0244415 A1 * | 10/2011 | Batesole | ................. | A61C 7/00 |
| | | | | 433/24 |
| 2014/0122027 A1 * | 5/2014 | Andreiko | ............... | A61C 7/002 |
| | | | | 703/1 |
| 2014/0247260 A1 * | 9/2014 | Ghoneima | ............. | G06T 19/00 |
| | | | | 345/419 |

* cited by examiner

PROCEDURE FOR DENTAL AESTHETIC ANALYSIS OF THE SMILE AREA AND FOR FACILITATING THE IDENTIFICATION OF DENTAL AESTHETIC TREATMENTS

This patent relates to dentistry and the aesthetic analysis of the teeth and smile, the role of supporting the dentist in the assessment and identification of possible dental and facial treatments from the aesthetic standpoint, and a valuable aid for the construction of dental prostheses. In particular, it describes a new method for the rapid and brief aesthetic assessment of the current state of the patient being examined and outlines the identification of the dental and orthodontic treatments most suited to improve the existing situation.

The method consists of a set of pre-defined steps, organized in a specific manner: special mathematical, statistical and logical algorithms supported by known scientific research which provide the result described above. This method can be integrated into dedicated software applications coded with different computer languages, preferably based on architectures using a single provider connected with multiple user clients according to the DAAS and HAAS concept.

In the current state of the art, the dental professional, who is preparing to formulate a proper treatment plan for a patient who needs cosmetic dental rehabilitation, begins a long journey of diagnostic considerations and a case study based on his/her personal knowledge in order to plan a series of treatments designed to rehabilitate the teeth of patients with dysfunctions, misalignments, malocclusions, blemishes, and other situations that require such treatments.

Each dentist decides on and plans the interventions independently or in collaboration with other dentists or orthodontists and other professionals, building on his/her experience, his/her knowledge, his/her ability to synthesize, his/her diligence, on the organizational capacity of his/her staff, and on the application of the best scientifically recognized methodologies in relation to the specific case.

Thus the evaluation of the interventions to be performed is discretionary and determined on a case by case basis. The technological assistance which the average dentist can rely on at present is limited to x-rays, digital photographs, plaster moulds of upper and lower teeth, and diagnostic wax-up performed in the laboratory by the dental technician upon request of the dental professional.

The appearance of the teeth is universally recognized as essential, even by the WHO, and is an essential condition for the psychophysical well-being of people and their social and relational dynamics. A set of specific interventions is designed to improve the aesthetic appearance of the teeth of the patient.

The appearance of a patient's smile is in part objective, such as crooked or misaligned teeth, abnormal teeth, gingival defects, models described in the scientific literature, etc., and in part subjective, regarding that which is included in the patient's perception of "flaw/disharmony" and the artistic perception of the dentist and dental technician.

While for the objective factors a series of interventions have been consolidated and described in industry guidelines, for the subjective factors the type, number and modalities of intervention are established by the dentist each time based on his/her personal experience, on his/her specific preparation, his/her strong artistic sense, and the possibility of consulting with other dentists, orthodontists and dental technicians as well as his/her ability to interpret the results desired by the patient.

The complexity of this approach requires today's professionals to conduct a preliminary study or "aesthetic project" that makes it possible to limit assessment errors until the implementation of simulation models intended to test both the functional and the aesthetic effect.

For each case, the dentist must repeat a series of complex medical, functional, technical, mechanical, psychological and aesthetic evaluations, all of which contribute to reaching the final result. This approach can have a predictable uncertain outcome having, in general, a significant average margin of error.

Thus the specialist assessments mentioned above require a lot of time, a lot of experience, strong intuition, great artistic sense, very specific preparation, and the effectiveness of the project depends to a large extent, referring to an average dentist, on consultation with other specialized professionals in the field and especially with the dental technician.

In this scenario, the dental technician often works far from dental offices and frequently does not have sufficient elements to perform individualized simulations for a specific patient, and consequently is forced to develop the aesthetic simulation based on intuition alone.

The main simulation used by average dentists is the diagnostic wax-up, that is, a wax simulation on a plaster model of the patient's teeth performed by a dental technician. This diagnostic wax-up is often performed on the brief indications of an orthodontist, which do not include the variety of aesthetic aspects recognized as crucial by the scientific community. If this were done with the means at our disposal today, a multiple page prescription/report would not be sufficient and the dentist's clinical assessment would take a very long time. Thus today, and by almost all operators, the diagnostic wax-up simulation is evaluated outside the aesthetic context of the patient's face, with brief summary information, and therefore is often approximate.

The quest to transfer as much information as possible to the dental laboratory, such as face bow record, measurements, models, pictures, etc., is currently still deficient as it is based on the concept that it is the dental technician who has to prepare the aesthetic simulation suitable for the patient's needs. This may not be plausible because it is exclusively the professional who must personally and knowingly design the aesthetic dental rehabilitation and then transmit all the necessary information to the dental technician, ensuring full cooperation in order to obtain a product according to prescription.

Due to the complexity of the knowledge presently required of the dentist, there is no existing system that can synthesize such a large aesthetic data set regarding the smile in just a few aesthetic dental measurements and succeed in giving brief instructions regarding treatment aimed at improving the smile.

Today there are methods that have only graphic and manual image processing functions, or which have partial calculation functions limited only to the resolution of just a few aesthetic parameters, and in any case they are insufficient aids for the full processing of a clinical case oriented to aesthetic dental rehabilitation.

There are known methods and computer programs intended to determine the orthodontic movements of the teeth in order to realign them correctly, there are known methods and software intended to determine the aesthetic golden ratio, and there are known methods and programs intended to perform simulations of surgical implants, but all have marginal and incomplete utility that still requires special study and preparation by the dentist.

As described so far, currently the overall assessment is left completely to the high level of preparation of the dentist and dental technician, with the resulting possible inaccuracy and partial analysis provided by the average dentist.

The subject of the present patent is a novel method for the aesthetic analysis of the teeth and smile, intended to support the dentist in the identification of flaws even if not apparently visible and in the identification of possible dental and orthodontic treatments in terms of aesthetics.

One objective of the new method is to normalize the interventions to be performed on the basis of a given number of specific parameters, about 270, scientifically supported by known research and detectable on the patient's teeth and face.

Another objective of the new method is to standardize in an objective manner the measurements and the evaluations of the patient's teeth in order to determine the precise current situation and the specific actions to undertake through the mechanisms of interactivity in a well-structured manner, not favouring pre-established methods or measures and with complete traceability of each of the decisions made by the user.

A further object of the new method is to include an educational and instructive aspect, inserted in the system, aimed at professionals in the field of aesthetic dentistry. In fact, potential users favour involvement for the purpose of obtaining an integrated system. This strengthens and puts into practice the definition of a new professional: the "cosmetic dentist".

Yet another objective of the new method is to allow the dentist, through the computer and the internet, to electronically share tests carried out on patients with other professionals and operators, such as dental technicians, even in opposite parts of the world, for various actions or stages of preparation such as consultations, preparation of diagnostic wax-ups, mock-ups, prostheses and creation of easily downloadable files without the need for physical transfers or in-person consultations. This sharing respects the privacy of the subject being examined through a system of division of data between the central server system, the so-called "cloud", and the user's client.

Still another objective of the new method is to allow the dentist to better determine the most appropriate interventions to achieve the desired result as a function of the subjective parameters, in relation to the face and character of the patient, recognized as significant with respect to the aesthetic appearance of the teeth.

Another objective of the invention is to provide an innovative new method that synthetically calculates the ideal aesthetic measurements of the teeth of the patient, the ideal vestibular extension and palatal position of the upper front teeth, the possible dominance of the maxillary central incisors and the symmetry through an algorithmic elaboration of all the acquired data, of all the results of the calculation of the aesthetic parameters involved as a function of the programmed criteria. This algorithm is a cascade of calculations processed according to a "cognitive processing" structured method of interdependence with a configuration that simulates the human reasoning of an experienced professional. The interactivity of the dentist-user, implemented and limited to a few variables that reflect the exclusively discretionary nature of the user's decision, creates an indispensable qualitative leap in dental diagnostics and in "smile design".

These and other direct and complementary objects are achieved by the new process for aesthetic analysis and for the identification of dental and orthodontic treatments, including:
  digital photos of the teeth and face of the patient according to an established series of poses and shots;
  calibration of those images according to certain measurements made directly on the patient's teeth and face;
  identification, on those calibrated images, of a set of characteristic reference points called landmarks;
  analysis of the current state from the aesthetic perspective and parameterization of the images with respect to the characteristic reference points as a function of the significant parameters commonly and scientifically recognized as crucial for the aesthetic appearance of the teeth and face;
  user interactivity in the formulation of the results and consequent learning enrichment;
  exchange of information, whether images or anatomical measures, with other specialized professionals for consultations or dental technicians for the preparation of corrective measures and/or prostheses;
  identification of possible treatments to achieve aesthetic improvement;
  simulation of the possible final result which may be obtained with the treatments identified;
  presentation of the possible final result which may be obtained on the patient to facilitate communication, compliance, and informed awareness of this possible end result.

The new process leads to the concise, intelligent and quick processing of a comprehensive study of the smile of a patient on digital photos defined and calibrated in relation to more than 270 aesthetic parameters for statistical reference of scientific origin and through the subjective evaluation made by the specialist user, with the possible cooperation with another medical or dental team.

The new process comprises a series of original algorithms that simulate with considerable accuracy the human reasoning of the expert practitioner in developing and synthesizing artistic perceptions, in the analysis of cephalometric proportions, in the analysis of more than 270 aesthetic parameters with known scientific references, in the processing of complex and intuitive rules that would take days or weeks of work.

The new method involves processing of data collected on a defined series of calibrated digital photos, x-rays, and subjective questions addressed to specialist users from the field. Then, a logical and numerical process is developed through an algorithmic system that simulates human reasoning.

The end result is the automatically calculated description of the current aesthetic state of the patient's smile in relation to the calculation of ideal aesthetic measurements of the teeth and proposes possible specialist treatments aimed at creating a customized ideal smile.

The new method, which can be used for the development of dedicated software applications using different computer languages, makes use of a corresponding computer, to guide the operator in the various stages of inquiry, such as the directions for the procedures used to acquire images of the patient, to obtain specific measurements on the images previously acquired and parameterised, and to develop and propose possible treatments to achieve the desired aesthetic improvement.

The new method makes it possible to concisely calculate the ideal measures of the patient's teeth and to indicate the ideal vestibular extension and palatal position of the upper front teeth, the possible dominance of the upper central incisors and the symmetry intended to re-calibrate the ideal measures according to programmed criteria.

The new method provides for the concise calculation of the ideal measures of the teeth using data obtained from the results of the aesthetic parameters calculated by the system through their individual algorithms, parameter by parameter, and from input in the set of data entered in the process such as initial measures of teeth, face, age, race, character and so on.

The new method provides for the processing of a large number of aesthetic parameters of the face and teeth together, creating interdependencies between them, which is not achievable in a short time with the known methods, and synthesizes them into concrete measures.

The new method involves the performance of a cascade of calculations with a certain type of applied functions and runs on the basis of logical and scientific criteria supported by current literature.

The photographs of the teeth and the X-rays of the patient are taken at the outset.

This photographic examination is carried out using pre-established criteria and expressions which are explained in an easy to understand user's guide.

The images are taken in defined poses such as:
mouth with teeth closed (teeth with mouth gag),
mouth with teeth closed in left and right lateral view, with or without the aid of mirrors,
surface of upper and lower teeth,
occlusal (with the aid of mirrors),
smile with teeth closed (view of just the mouth with the lips and base of the nose),
view of mouth forming phoneme "f" or "v",
mouth and base of the nose with a full smile,
face with open smile,
face with smile with teeth closed,
profile of smile with teeth closed,
face with lips closed,
profile with lips closed,
three quarters of face with smile with teeth closed,
mouth with teeth closed in head-to-head (view of mouth only with lips and root of the nose),
lateral tele-X-ray,
view of mouth forming phoneme I or E (view of mouth only with lips and base of the nose),
lips relaxed (view of the mouth only with lips and base of the nose, lips not touching, slightly open, and muscles released),
orthopantomography image,
juxta-gingival X-ray image,
image of upper teeth and colours in scale.

Multiple images of the patient in the same positions are preferable.

These images are calibrated, either individually or in relation to one another, as a function of some actual measurements recorded directly on the patient. Calibration is a known technique that allows the coefficient of proportionality between the images and the actual measurements to be stored.

Since the professional user may, at times, do this operation incorrectly, an original method that seeks the images' calibration reliability percentage is implemented.

The user then decides autonomously whether it is necessary to double check everything, repeat the calibration, or continue the test.

Once the images have been calibrated and parameterized, it is possible to record on them all the remaining necessary measures, such as the height of each tooth, the length of the labial commissure, the total height of the lips, the distance between the subnasal point and the chin, etc.

According to the invention, the computer and the corresponding program guide the professional user in the detection and determination of all these measures, both with graphical representations, possibly animated next to the image of the patient, and with explanations and indications of the reference points between which to make automatic or manual measurements, called landmarks.

The set of direct or indirect measurements recorded on the images are processed by means of algorithms and tables, thus making it possible to determine the exact current status of the patient in question, parameter by parameter.

The comparison between the measurements and the parameters of the current state of the patient and the parameters indicated in stored tables resulting from consolidated literature enable the determination of one or more recommended treatments and/or interventions to improve the appearance of the patient's smile.

A two-dimensional and/or three-dimensional simulation of the patient's teeth following the suggested treatments and/or interventions is included, in order to enable professional users and patient users to imagine the possible final result through the use of "model" teeth libraries in a digital format or to use the files to proceed autonomously with known photo editing tools not provided by the system to alter the images for a preview.

Both the images and measures collected and the specific indication of suggested treatments and/or interventions can be sent to or shared with other professionals, such as dentists, orthodontists and dental technicians for any further consultation.

In the same way, the measures collected can be sent to a dental technician who, by means of the automatic selection of a 3D and 2D digital library of teeth similar to those resulting from the processing provided by the system, through a selection from the database, can proceed to the digital implementation and prototyping, with CAD-CAM models or stereolithography, of a physical model of the possible final result already displayed on the screen.

Sending files to the dental technician who shares the dedicated software with the reference dentist thus creates the conditions to perform prosthetic dentistry modelling at a distance and to receive a file of the finished modelling or a physical simulation such as, for example, a diagnostic wax-up, mock-ups, etc., sent by post.

The simulation(s) made in this manner, upon the dentist's indication/prescription, can be viewed by the patient to facilitate communication, compliance and informed awareness of the possible final result.

The drawings constitute a part of this specification and include exemplary embodiments of the invention, which may be embodied in various forms, as follows.

A preferred embodiment of a software program for the new method is described here below, with reference to the drawings attached by way of non-limiting example.

Figure 1:
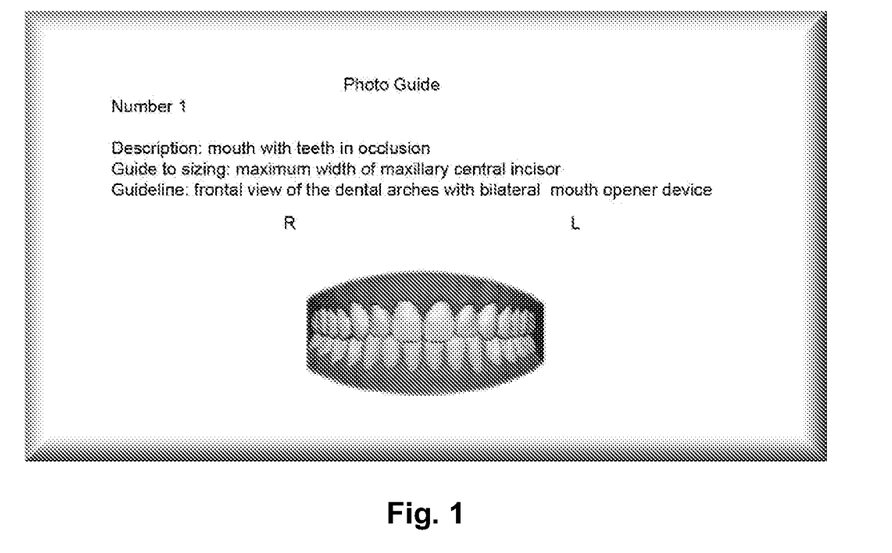
FIGS. 1 and 2 are exemplary photographic guide images providing information for proper photographing in a procedure according to the invention.
Figure 2:
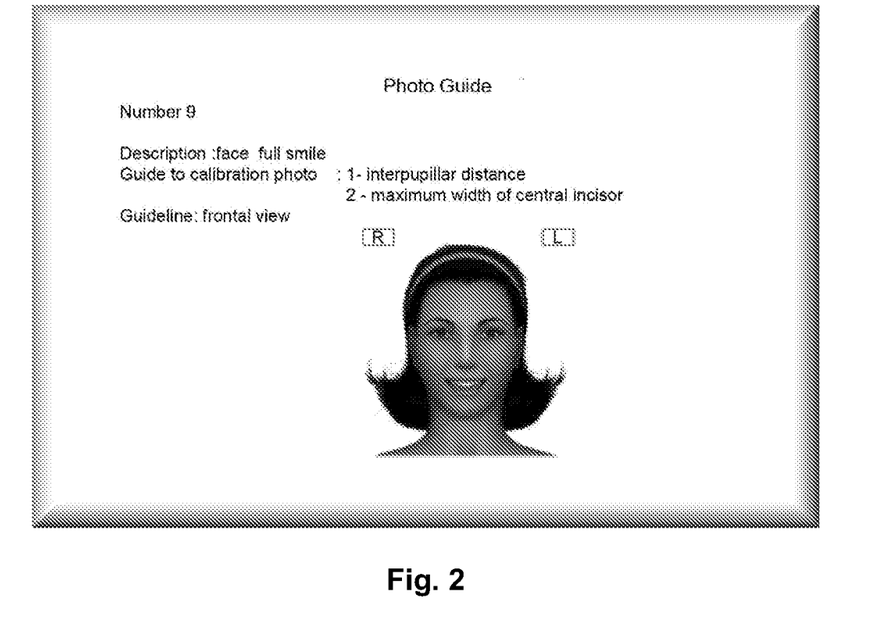

FIGS. 1 and 2 show two sample photographic guide images, integrated in the program, designed to provide all the information necessary to properly take the required photographs.

Figure 3:
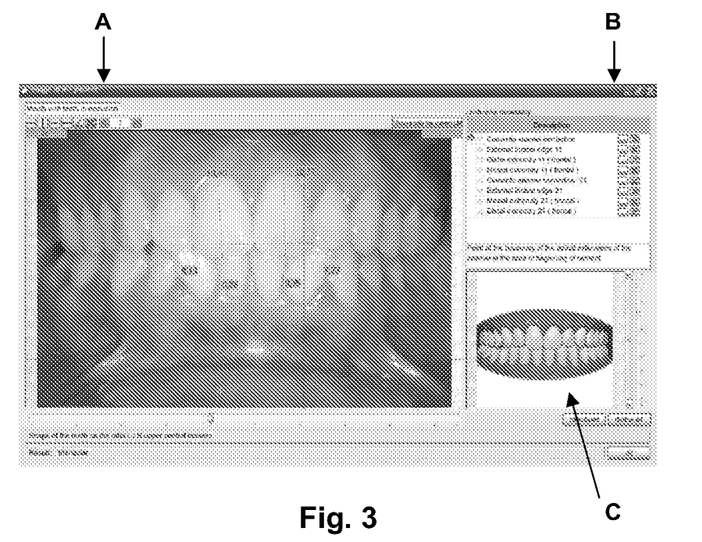
FIGS. 3 and 4 illustrate exemplary measurements and parameterization of a patient's teeth in a procedure according to the invention.
Figure 4:
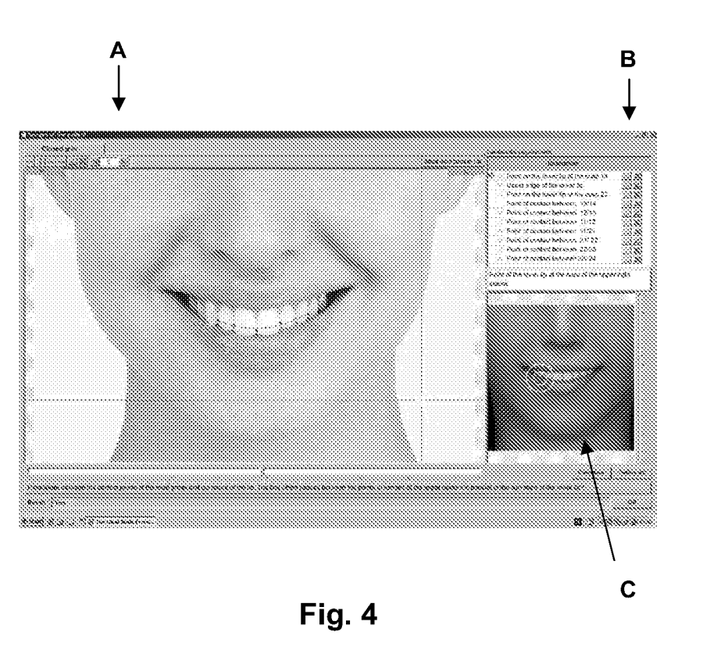

FIGS. 3 and 4 show two examples of the measurement and parameterisation of the patient's teeth.

On one side (A) the various photos of the patient, in relation to the parameter which must be recorded or verified, are displayed.

Displayed on the opposite side (B) is the text related to the highlighted parameter, with questions or information regarding measurements involving a subjective response.

This subjective function is optional for almost all parameters, so that the user, if he/she is not in agreement, can interactively change the results of the calculation of the parameters, recording the change event.

In addition, demonstration images (C) are displayed that help the user focus on the concept of the parameter in question.

On each one of these images of the patient reference points are recorded relative to the parameter to be measured. The measure is calculated automatically according to the points indicated and the previously calibration parameters set for the individual image.

Figure 5:
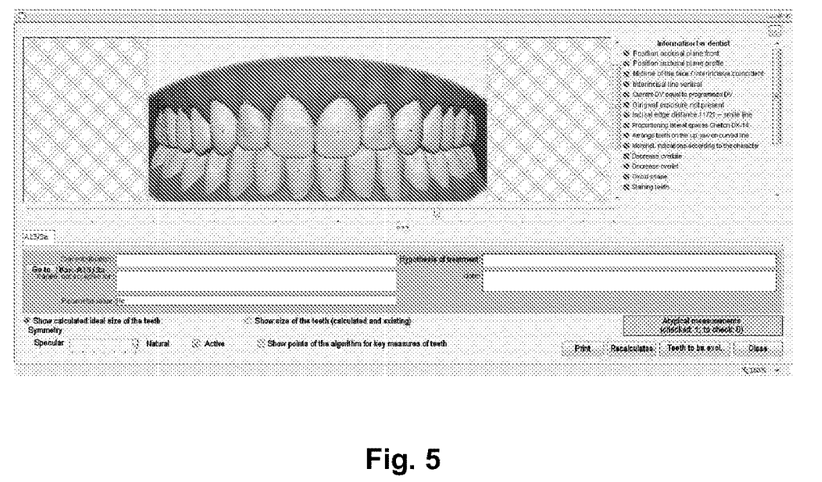
FIG. 5 illustrates a display of individual parameters of a patient, together with the patient's current status/diagnosis and instructions or recommendations for treatment.

The result of each individual parameter is displayed, together with the patient's current status/diagnosis and the instructions or recommendations for treatment, as shown in FIG. 5.

It is possible to add notes, as a reminder for the dentist, as a note intended for the user patient, or as indications for the dental technician.

Access to the bibliography concerning the parameter in progress is also available, so that it is possible to see the source and the reference literature for the algorithmic construction of that specific parameter.

Figure 6:
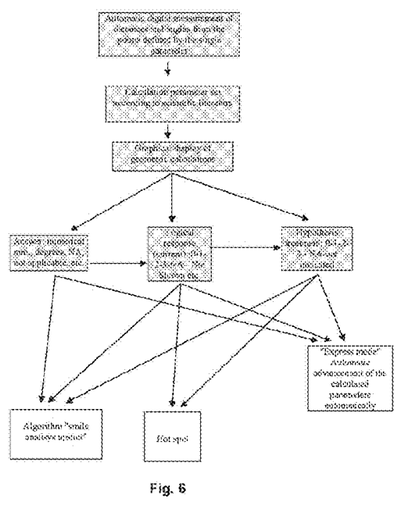
FIG. 6 illustrates diagramatically sequences of aesthetic analysis and identification of dental and orthodontic treatments in a procedure according to the invention.

FIG. 6 shows the diagram of logical sequences of the novel method for aesthetic analysis and identification of dental and orthodontic treatments.

Figure 7:
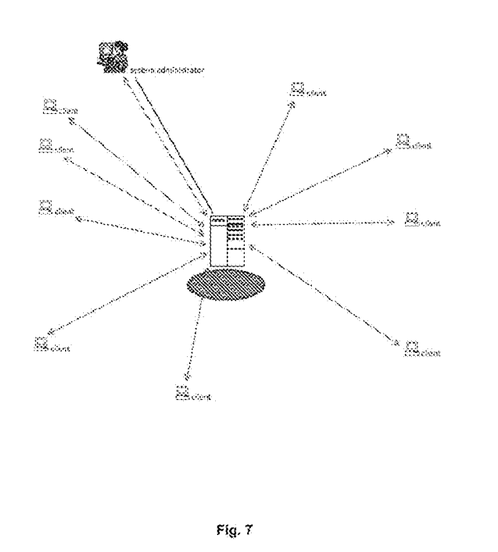
FIG. 7 illustrates diagramatically a system architecture for a procedure according to the invention.

FIG. 7 shows a diagram of the system architecture of the new method.

The method constituted as described above presents considerable advantages.

The new method enables the precise definition of the current state of the patient examined in terms of the aesthetics of the smile.

The new method facilitates the development of the possible recommended treatments which are designed to improve the functional appearance of the smile.

The new method enables the fast synthesis of a selection of ideal measures of the teeth as a function of the face and personality.

The new method enables the synthesis of some basic indications for aesthetic rehabilitation addressed to the dentist, the dental technician, and the specialist team.

The new method makes it possible to exploit the data usable for the processing of a graphic simulation to directly involve the patient so as to make the communication of a hypothetical final result effective.

The present invention also allows the selection of a digital library of model teeth in appropriate three-dimensional files that, in addition to enabling simulations, facilitates the construction and verification, through rapid prototyping, of a three-dimensional model that can be manipulated graphically by the dental technician in order to make prostheses or develop feasibility studies.

The new process enables the production of synthetic directions that are essential for the dental technician for the simple and rapid construction of prototypes and simulations of any type.

The new method allows the detailed prescription to be sent also electronically in a file so that the professional can collaborate with dental technicians and colleagues around the world.

These are the basic outlines of the process that are sufficient for the skilled person to implement the invention, consequently, the practical application may include variations without prejudice to the substance of the innovative concept expressed herein.

Therefore, with reference to the preceding description and the attached drawings, the following claims are made.

The invention claimed is:

1. A method of electronic analysis of teeth in a smile area, suited to facilitate identification of aesthetic dental treatments, comprising:
   performing a photographic examination of a patient's teeth according to an established series of poses and shots to generate digital images;
   electronically calibrating said digital images as a function of predetermined measures taken directly on the patient's teeth and/or face;
   performing a computer-assisted analysis of consistency of input data, such to intercept and limit errors due to incorrect measurements of actual data on the patient's teeth and/or face in order to calibrate the digital images;
   identifying, on said calibrated images, a defined set of characteristic reference points called landmarks or reference points and displaying said characteristic reference points on a computer display;
   causing an automatic electronic analysis and parameterization of said digital images, either individually or all together, with reference to said characteristic reference points as a function of significant parameters commonly recognized as decisive for aesthetic appearance of teeth;
   determining possible treatments to achieve a desired aesthetic improvement, parameter by parameter, with appropriate logical and numerical responses;
   performing a two- or three-dimensional electronic simulation of the patient's teeth that includes the desired aesthetic improvement; and
   screening and/or printing a complete report of said possible treatments.

2. The method according to claim 1, wherein poses and shots of the photographic examination comprise one or more of the following:
   mouth with teeth closed;
   left and right lateral view of mouth with teeth closed;
   upper and lower teeth;
   occlusal surface;
   smile with teeth closed;
   view of mouth forming phoneme "f" or "v";
   mouth and base of nose with a full smile;
   face with open smile;
   face with smile with teeth closed;
   profile of smile with teeth closed;

face with lips closed;
profile with lips closed;
three quarters of face with smile with teeth closed;
mouth with teeth closed in head-to-head;
lateral tele-X-ray;
view of mouth forming phoneme I or E;
lips relaxed;
orthopantomography image;
juxta-gingival X-ray image; or
image to scale with colors.

3. The method according to claim 1, wherein the step of electronically calibrating said digital images comprises processing measures including: h11, L11, h21, L22, L13, L23, h41, L41, base of nose, right pupil, left pupil, length of nose, or helix tragus.

4. The method according to claim 1, further comprising the step of identifying possible final result obtainable with identified treatments by determining a graphic and text summary of possible treatments recommended to achieve a desired aesthetic improvement with a graphic support and synthetic and schematic descriptions of critical treatments.

5. The method according to claim 1, further comprising the step of computer-assisted analyzing results of parameters already calculated in order to synthesize ideal measures of the teeth involved in a smile.

6. The method according to claim 1, further comprising the step of employing an algorithm, which synthesizes ideal dental measures and simulates human reasoning of an experienced professional in processing and synthesizing one or more artistic perceptions, critical experience, analysis of cephalometric and dental proportions, or critical analysis of the aesthetic parameters already calculated, starting from said images and initial inputs.

7. The method according to claim 1, further comprising the step of providing an electronic graphic representation of measures resulting from the analysis, comparing obtained data in an immediate way with original data and allowing computer-assisted interactive modification of symmetry or of height of the teeth and a consequent relationship with the teeth using a computer cursor on a display with a graduated scale, with which a user can balance, within certain limits, height of central incisors, wherein a movement of the computer cursor changes an automatic calculation of measures, interfering with a synthesis algorithm in order to recalculate a result regarding all the teeth depending on the interactive modification.

8. The method according to claim 1, further comprising the step of providing a controlled and authorized sharing of information, whether of the digital images or anatomical measures, with other specialized professionals and/or dental technicians, both for preparation of corrective devices and/or prostheses, and to entrust execution of some steps of the method to other organizations.

9. The method according to claim 1, further comprising the step of providing instruments suited to determine linear, angular, or curved measures, or measures of any other nature, on the calibrated images.

10. The method according to claim 1, further comprising the step of enabling a learning of basics for professional training oriented toward cosmetic dentistry through guided descriptions of reference images and user guides with auto scroll on a computer display for each parameter and literature reviews related to each parameter or group of parameters.

11. The method according to claim 1, further comprising the step of using data resulting from processing to edit by photo-retouching with computer applications on the images of the patient being examined.

12. The method according to claim 11, further comprising the step of using the edited digital images to perform thereon respectively measurements and analysis of the parameters of a smile.

13. The method according to claim 1, further comprising the step of providing obtained data as digital files of two-dimensional images and/or three-dimensional shapes catalogued by similar values, wherein said digital files of two-dimensional images and/or three-dimensional shapes are arranged to be supplemented with additional information by a professional user.

* * * * *